United States Patent
Veeneman et al.

(10) Patent No.: US 6,756,375 B2
(45) Date of Patent: Jun. 29, 2004

(54) 10-ARYL-11H-BENZO[B]FLUORENE DERIVATIVES AND ANALOGS FOR MEDICINAL USE

(75) Inventors: Gerrit Herman Veeneman, Schaijk (NL); Hubert JanJozef Loozen, Uden (NL); Jordi Mestres, Central Scotland (GB); Eduard Willem De Zwart, Schaijk (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 10/362,555

(22) PCT Filed: Aug. 17, 2001

(86) PCT No.: PCT/EP01/09500

§ 371 (c)(1),
(2), (4) Date: Jul. 24, 2003

(87) PCT Pub. No.: WO02/16316

PCT Pub. Date: Feb. 28, 2002

(65) Prior Publication Data

US 2004/0059004 A1 Mar. 25, 2004

(30) Foreign Application Priority Data

Aug. 23, 2000 (EP) .............................................. 00202945

(51) Int. Cl.[7] ...................... C07C 321/28; C07C 43/23; A61K 31/05; A61P 5/06; C07D 295/08
(52) U.S. Cl. .................... 514/238.8; 514/730; 514/765; 544/154; 544/294; 544/357; 546/195; 546/285; 548/528; 548/160; 568/812; 568/817; 568/719; 568/633; 549/365; 564/280
(58) Field of Search ................................ 514/730, 765, 514/238.8; 568/812, 817, 719; 544/154, 294, 357; 546/195, 285; 548/528, 160; 549/365; 564/280

(56) References Cited

FOREIGN PATENT DOCUMENTS

| EP | 0733620 A | * | 9/1996 |
| EP | 0832881 A | * | 4/1998 |
| EP | 0873992 A | * | 10/1998 |
| WO | 9619458 A | * | 6/1996 |
| WO | 01 72713 A | | 10/2001 |

\* cited by examiner

*Primary Examiner*—Robert W. Ramsuer
*Assistant Examiner*—Andrea D. Small
(74) *Attorney, Agent, or Firm*—Mark W. Milstead

(57) ABSTRACT

The invention provides for a non-steroidal compound having the formula

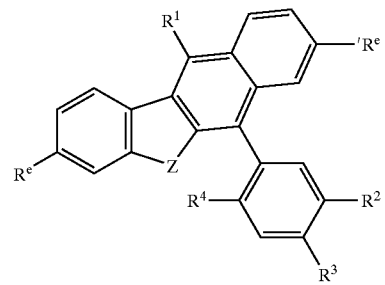

wherein $R^e$ and $'R^e$ are OH, optionally independently etherified or esterified; Z is —$CH_2$— or —$CH_2CH_2$—; $R^1$ is H, halogen, $CF_3$, or (1C–4C)alkyl; $R^2$, $R^3$ and $R^4$ are independently H, halogen, —$CF_3$, —$OCF_3$, (1C–8C)Alkyl, hydroxy, (1C–8C)alkyloxy, aryloxy, aryl(1C–8C)alkyl, halo(1C–8C)alkyl, —$O(CH_2)_mX$, wherein X is halogen or phenyl and m=2–4; —$O(CH_2)_mNR_aR_b$, —$S(CH_2)_mNR_aR_b$ or —$(CH_2)_mNR_aR_b$, wherein m=2–4 and $R_a$, $R_b$ are independently (1C–8C)alkyl, (2C–8C)alkenyl, (2C–8C)alkynyl, or aryl, optionally substituted with halogen, —$CF_3$, —$OCF_3$, —CN, —$NO_2$, —OH, (1C–8C)alkoxy, aryloxy, carboxyl, (1C–8C)alkylthio, carboxylate, (1C–8C)alkyl, aryl, aryl(1C–8C)alkyl, halo(1C–8C)alkyl or $R_a$ and $R_b$ form a 3–8 membered ring structure, optionally substituted with halogen, —$CF_3$, —$OCF_3$, —CN, —$NO_2$, hydroxy, hydroxy(1C–4C)alkyl, (1C–8C)alkoxy, aryloxy, (1C–8C)alkylthio, carboxyl, carboxylate, (1C–8C)alkyl, aryl, aryl(1C–8C) alkyl, halo(1C–8C)alkyl. The compounds can be used for the preparation of a medicine, in particular for use in estrogen-receptor-related treatments.

10 Claims, No Drawings

10-ARYL-11H-BENZO[B]FLUORENE DERIVATIVES AND ANALOGS FOR MEDICINAL USE

FIELD OF THE INVENTION

The invention relates to a non-steroidal compound with affinity for estrogen receptors and to a method for selective estrogen receptor modulation (SERM) with such a compound and to the use of such a compound for the manufacture of a medicine for estrogen-receptor-related treatments.

BACKGROUND OF THE INVENTION

Compounds with affinity for estrogen receptors have found long-standing utility in the treatment of a variety of medical indications and in regimes for contraceptive purposes. Despite the long history of the field there still is a need for more effective, safer and more economical compounds than the existing ones. This need is the more pressing in view of advancement in health care in other areas, which has led to an increasingly longer life span. This is in particular a problem for women for whom the decline in estrogenic hormones at menopause is drastic and has negative consequences for bone strength and cardiovascular functions. For the control or prevention of estrogen sensitive tumor growth, compounds are needed which are antagonists, partial antagonists or tissue selective agonists for estrogen receptors.

The discovery of subtypes of estrogen receptors, there being an α-subtype (ERα) and a β-subtype (ERβ) of such receptors (Mosselman et al., *FEBS Letters* vol. 392 (1996) pp. 49–53 as well as EP-A-0 798 378), offers the possibility to influence one particular subtype of those two receptors more selectively, immanently resulting in more effective treatments or treatments with less side effects. Since these receptors have a different distribution in human tissue, the finding of compounds which possess a selective afinity for either of the two is an important technical progress, making it possible to provide a more selective treatment in estrogen-receptor related medical treatments, such as those for contraception and for treatment of menopausal complaints, osteoporosis, and estrogen dependent tumour control, with a lower burden of estrogen-related side-effects.

This invention pertains to non-steroidal estrogenic compounds with a 10-aryl-11H-benzo[b]fluorene or a 7-aryl-5,6-dihydrobenz[a]anthracene skeleton. Compounds with a 10-phenyl-11H-benzo[b]fluorene skeleton are described as products from enediyne thermocyclisation [Schittel, M., Z. *Naturforsch, B: Chem. Sci.* (1998), 53, 1015–1020] and from [4+2] cycloaddition reactions of diarylacetylenes [Rodriguez, D., *Org. Lett.* (2000), 2, 1497–1500], but no medicinal activity of these compounds is known. Indeno[1,2-g]quinolines with interactions with nuclear receptors are disclosed in WO 96 19458. Despite the keen interest in compounds with affinity for the estrogen receptor, new compounds with a 10-aryl-11H-benzo[b]fluorene or 7-aryl-5,6-dihydrobenz[a]anthracene skeleton and affinity for the estrogen receptor cannot be learnt from these documents.

SUMMARY OF THE INVENTION

The present invention resides in the finding that compounds with an unsaturated or partially unsaturated four-ring skeleton with hydroxyl substitutions at specific locations, i.e. 2,8-dihydroxy-10-aryl-11H-benzo[b]fluorene and 3,9-dihydroxy-7-aryl-5,6-dihydro-benz[a]anthracene, possess surprisingly high antagonism for ERβ. Some of these compounds also show ERα antagonism or ERα agonism.

DETAILED DESCRIPTION OF THE INVENTION

Specifically, the invention provides non-steroidal compounds having the formula 1

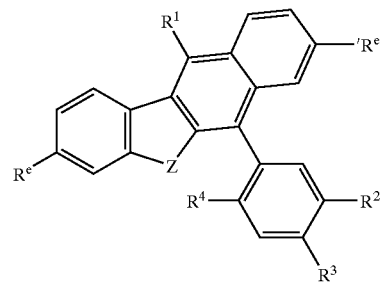

Formula 1 wherein:

$R^e$ and $'R^e$ are OH, optionally independently etherified or esterified;

Z is —$CH_2$— or —$CH_2CH_2$—;

$R^1$ is H, halogen, $CF_3$, or (1C–4C)alkyl;

$R^2$, $R^3$ and $R^4$ are independently H, halogen, —$CF_3$, —$OCF_3$, (1C–8C)Alkyl, hydroxy, (1C–8C)alkyloxy, aryloxy, aryl(1C–8C)alkyl, halo(1C–8C)alkyl, —$O(CH_2)_m X$, wherein X is halogen or phenyl and m=2–4; —$O(CH_2)_m NR_a R_b$, —$S(CH_2)_m N_a R_b$ or —$(CH_2)_m NR_a R_b$, wherein m=2–4 and wherein $R_a$, $R_b$ are independently (1C–8C)alkyl, (2C–8C)alkenyl, (2C–8C)alkynyl, or aryl, optionally substituted with halogen, —CF3, —OCF3, —CN, —$NO_2$, —OH, (1C–8C)alkoxy, aryloxy, carboxyl, (1C–8C)alkylthio, carboxylate, (1C–8C)alkyl, aryl, aryl(1C–8C)alkyl, halo(1C–8C)alkyl or $R_a$ and $R_b$ form a 3–8 membered ring structure, optionally substituted with halogen, —CF3, —$OCF_3$, —CN, —$NO_2$, hydroxy, hydroxy (1C–4C)alkyl, (1C–8C)alkoxy, aryloxy, (1C–8C) alkylthio, carboxyl, carboxylate, (1C–8C)alkyl, aryl, aryl(1C–10 8C)alkyl, halo(1C–8C)alkyl.

Preferred compounds of the invention can be obtained by selecting —$CH_2$— for Z and hydrogen for $R^4$ in formula 1. For $R^1$ it is preferred to select compounds having H, halogen or $CF_3$. Compounds with $R^1$ in formula 1 is halogen, whereby chlorine is most preferred, are particularly potent and selective for the ERβ.

Another embodiment of the invention is a non-steroidal compound with a 10-Aryl-11H-benzo[b]fluorene skeleton having the formula 2

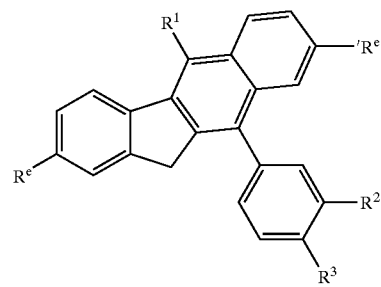

Formula 2 wherein:

$R^e$ and $'R^e$ are OH, optionally independently etherified or esterified;

$R^1$ is H, halogen or $CF_3$;

$R^2$ and $R^3$ are independently H, halogen, —$CF_3$, —$OCF_3$, (1C–8C)Alkyl, hydroxy, (1C–8C)alkyloxy, aryloxy, aryl(1C–8C)alkyl, halo(1C–8C)alkyl, —$O(CH_2)_m NR_a R_b$, —$S(CH_2)_m NR_a R_b$ or —$(CH_2)_m NR_a R_b$, wherein m=2–4 and $R_a$, $R_b$ are independently (1C–8C) allyl, (2C–8C)alkenyl, (2C–8C)alkynyl, or aryl, optionally substituted with halogen, —CF$_3$, —OCF$_3$, —CN, —NO$_2$, —OH, (1C–8C)alkoxy, aryloxy, carboxyl, (1C–8C)alkylthio, carboxylate, (1C–8C)alkyl, aryl, aryl(1C–8C)alkyl, halo(1C–8C)alkyl or $R_a$ and $R_b$ form a 3–8 membered ring structure, optionally substituted with halogen, —CF$_3$, —OCF$_3$, —CN, —NO$_2$, hydroxy, (1C–8C)alkoxy, aryloxy, (1C–8C)alkylthio, carboxyl, carboxylate, (1C–8C)alkyl, aryl, aryl (1C–8C)alkyl, halo(1C–8C)alkyl.

For compounds, having formula 3,

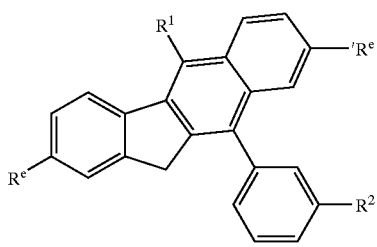

Formula 3 it is preferred to select those in which $R^e$ and '$R^e$ are OH, optionally independently etherified or esterified;

$R^1$ is H, halogen, CF$_3$;

$R^2$ is —O(CH$_2$)$_m$NR$_a$R$_b$, wherein m=2–3 and $R_a$, $R_b$ are independently (1C–5C)alkyl or (3C–5C)alkenyl, optionally substituted with OH or methoxy, or $R_a$ and $R_b$ form a 4–7 membered ring structure selected from the list: azetidine, pyrrolidine, 3-pyrroline, piperidine, piperazine, tetrahydropyridine, morpholine, thiomorpholine, thiazolidine, homopiperidine, tetrahydroquinoline and 6-azabicyclo[3.2.1]octane, which 4–7 membered ring structure can optionally be substituted with OH, methoxy, acetyl, carboxylate, (1C–3C)alkyl, phenyl, benzyl, and phenylethyl.

In particular, a very effective compound is made available by this invention by selecting a compound having formula 4:

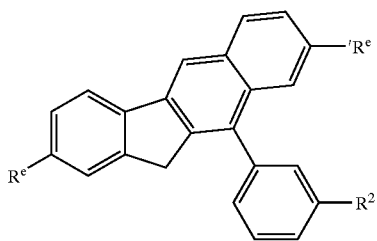

Formula 4 wherein:

$R^e$ and '$R^e$ are OH, optionally independently etherified or esterified;

$R^2$ is (3C–6C)alkyloxy, —O(CH$_2$)$_m$X (wherein X is halogen or phenyl and m=2–3), or —O(CH$_2$)$_m$NR$_a$R$_b$, (wherein m=2–3), whereby $R_a$, $R_b$ are independently (1C–5C)alkyl or (3C–5C)alkenyl, optionally substituted with OH or methoxy, or $R_a$ and $R_b$ form a 4–7 membered ring structure selected from the list: azetidine, pyrrolidine, 3-pyrroline, piperidine, piperazine, tetrahydropyridine, morpholine, thiomorpholine, thiazolidine, homopiperidine, tetrahydroquinoline and 6azabicyclo[3.2.1]octane, which 4–7 membered ring structure can optionally be substituted with OH, hydroxy(1C–2C)alkyl, methoxy, acetyl, carboxylate, (1C–3C)alkyl, phenyl, benzyl, and phenylethyl.

In those cases that the compound in formulas 1–4 contain a basic amine function, the compound may be used as a free base or as a pharmaceutically acceptable salt such as hydrochloride, acetate, oxalate, tartrate, citrate, phosphate, maleate or fumarate.

The ester and ether compounds in the collection of compounds according to the invention often have activity as prodrug. A prodrug is defined as being a compound which converts in the body of a recipient to a compound as defined by the formulas 1 to 4 and to the free hydroxyl compounds of the above defined compounds. Preferred ester and ether prodrugs are carboxylic acid esters or alkyl ethers on one or both hydroxyl groups, and more preferred prodrugs are (2C–6C)carboxylic acid esters, such as esters of (iso) butanoic acid, or (1C–4C) alkyl ethers. In general, the hydroxy groups can for example be substituted by allyl*oxy, alkenyl*oxy, acyl*oxy, aroyloxy, alk*oxycarbonyloxy, sulfonyl groups or phosphate groups, whereby the carbon chain length of the groups denoted with an asterisk (*) is not considered to be sharply. delimited, while aroyl generally will comprise a phenyl, pyridinyl or pyrimidyl, which groups can have substitutions customary in the art, such as allyl*oxy, hydroxy, halogen, nitro, cyano, and (mono-, or dialkyl*-)amino. The length of the alkyl, alkenyl and acyl groups is selected depending on the desired properties of the prodrugs, whereby the longer chained prodrugs with for example lauryl or caproyl chains are more suitable for sustained release and depot preparations. It is known that such substituents spontaneously hydrolyse or are enzymatically hydrolysed to the free hydroxyl substituents on the skeleton of the compound. Such prodrugs will have biological activity comparable to the compounds to which they are converted in the body of the recipients. The active compound to which a prodrug is converted is called the parent compound. The onset of action and duration of action as well as the distribution in the body of a prodrug may differ from such properties of the parent compound.

Substitution variants of the compounds of the present invention are possible for similar use. A substitution variant is defined to be a compound which comprises in its molecular structure the structure as defined by the formula I. The skilled person inspecting the group of compounds provided by the present invention will immediately understand that modification by a substituent to the skeleton can yield a compound with similar biological activity as the compound without this particular substituent. It is common practise in the art to test such substitution variants for the expected biological activity so that it is a routine skill to obtain useful substitution variants of compounds according to the invention.

Other terms used in this description have the following meaning:

alkyl is a branched or unbranched alkyl group, for example methyl, ethyl, propyl, isopropyl, butyl, sec-butyl, tert-butyl, hexyl, octyl, capryl, or lauryl;

alkenyl is a branched or unbranched alkenyl group, such as ethenyl, 2-butenyl, etc.;

alkynyl is a branched or unbranched alkynyl group, such as ethynyl and propynyl;

halogen refers to fluorine, chlorine, bromine and iodine;

aryl is a mono- or polycyclic, homo- or heterocyclic aromatic ring system, such as phenyl, naphtyl or pyridinyl; a monocyclic ring with 6 atoms is preferred for use;

a ring system or structure is referring to a chemical group in which all atoms are involved in formed rings, which rings can be saturated or (partially) unsaturated and comprise C, O, S or N atoms;

aroyl is arylcarbonyl such as a benzoyl group;

alkanoyl means a formyl or alkylcarbonyl group such as formyl, acetyl and propanoyl;

acyl is a (substituent-)carbonyl group, such as an aroyl or alkanoyl;

carboxyl is a —COOH substituent, making the compond an organic acid; carboxylate is an ester or salt of a carboxyl substituent.

The prefixes (1C–4C), (2C–4C) etc. have the usual meaning to restrict the meaning of the indicated group to those with 1 to 4, 2 to 4 etc. carbon atoms.

The estrogen-receptor affinity profile of the compounds according to the present invention, makes them suitable for use in estrogen-receptor related medical treatments, in the sense that these compounds are improved anti-estrogens, partial anti-estrogen, partial estrogens or selective (partial) (anti-)estrogens. Estrogen-receptor related medical treatments specifically named are those for contraception or for treatment or prevention of benign prostate hypertrophy, cardiovascular disorders, menopausal complaints, osteoporosis, estrogen dependent tumour control or central nervous system disorders such as depression or Alzheimer's disease. In particular those compounds which have selective affinity for the ERβ receptor are suitable for estrogen-receptor related medical treatments under diminished estrogen-related side-effects. This is most desirable when these compounds are used in the treatment of osteoporosis, cardiovascular disorders and central nervous system disorders such as depression or Alzheimer's disease. Selective blockade of ERβ-receptors with compounds of this invention can be used to prevent and reduce malignant tumor growth and hyperplasias. The receptor selectivity helps to effectuate tissue selectivity. Those tissues rich in ERβ-receptors can be protected by ERβ-receptor antagonists from the risk of stimulation of growth by estrogenic agonists. The latter can be of endogenous origin or from exogenous origine when administered during estrogenic treatment, for example for hormone replacement after menopause. Tissues that can benefit from protection in view of the presence of ERβ-receptors are prostate, testes (human), lung, colon and endometrium. In particular, endometrium proliferation can be reduced by ERβ antagonists of the invention.

The compounds of the invention can be produced by various methods known in the art of organic chemistry in general. More specifically the routes of synthesis as illustrated in the schemes and examples can be used.

Scheme 1
A general procedure that can be used to prepare compounds of the invention

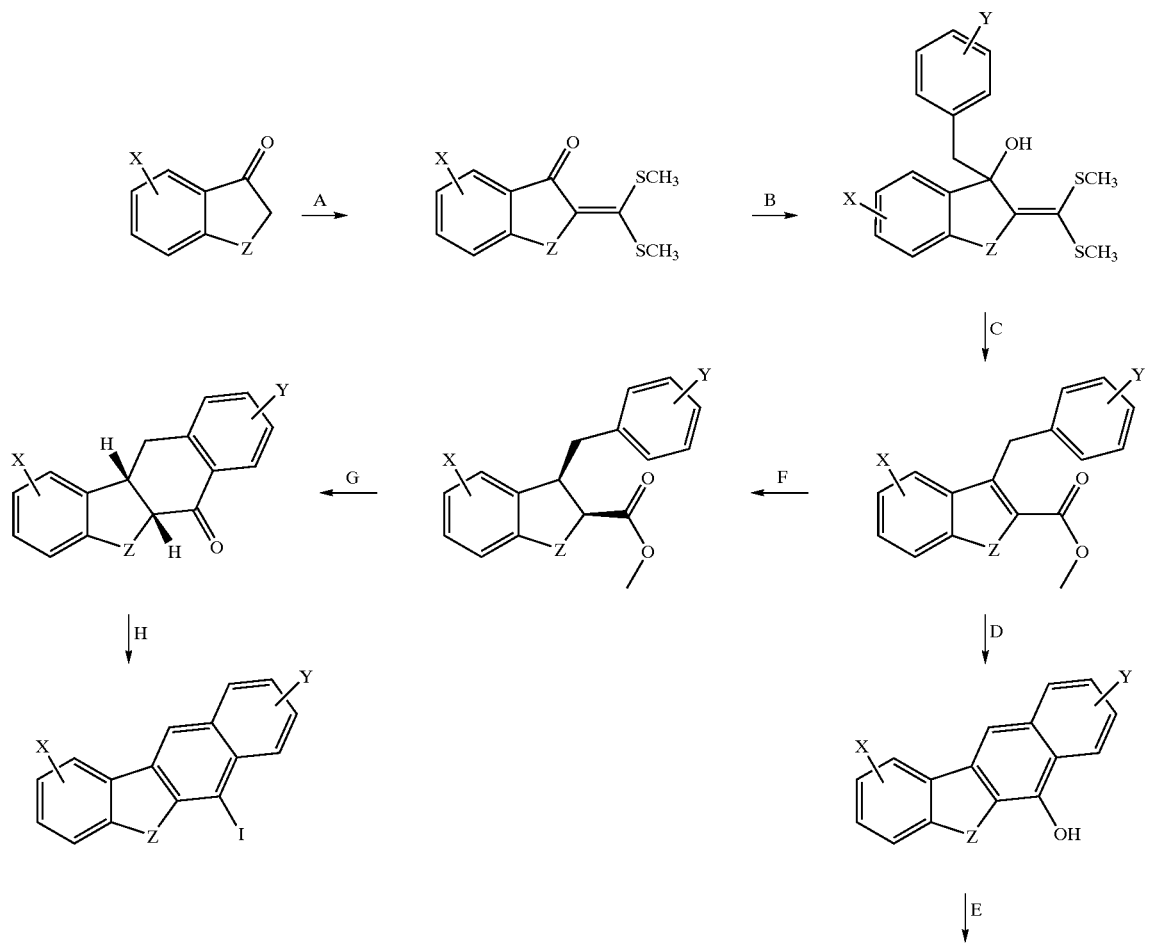

-continued

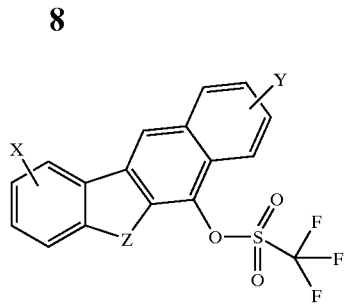

Z = CH₂ or CH₂CH₂
X, Y = OCH₃, occasionally accompanied by other substituents

Scheme 2

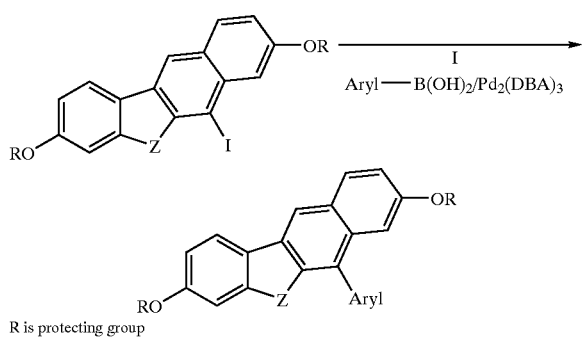

R is protecting group

With reference to scheme 1, the benzofluorene (Z=CH₂) and the benzanthracene (Z=CH₂CH₂) skeleton can be assembled in an identical manner. In step A adequately substituted indanones or tetralones are treated with CS₂ under appropriate basic conditions to introduce a dithioketene function (in fact serving as a carboxylate equivalent), after which procedure reaction with an organometallic derivative of a substituted benzylhalide (preferably a Grignard derivative) in step B, followed by alcoholysis (step C) leads to an α,β-unsaturated ester. At this stage an acid catalyzed cyclization (step D) immediately leads to the phenolic benzofluorene (or benzanthracene). Conversion of this into a reactive intermediate (like triflate) in step E allows the introduction of the desired functionalities (like aryl groups, carboxylates etc) by means of known organometallic techniques.

If the mentioned α,β-unsaturated ester is first hydrogenated in step F prior to cyclization (step G), the indicated ketones become available. They may be easily converted into the aromatic iodide in step H. These, under circumstances may be more reactive than the afore-mentioned triflates and provide valuable alternatives for finctionalization (step I in scheme 2).

Ester prodrugs can be made by esterification of compounds with free hydroxyl groups by reaction with appropriate acyl chlorides in pyridine. Free dihydroxy compounds having formula 1 can be made by hydrolysis of ether precursors.

The present invention also relates to a pharmaceutical composition comprising the non-steroidal compound according to the invention mixed with a pharmaceutically acceptable auxiliary, such as described in the standard reference Gennaro et al, Remmington: The Science and Practice of Pharmacy, (20th ed., Lippincott Williams & Wilkins, 2000, see especially Part 5: Pharmaceutical Manufacturing). Suitable auxiliaries are made available in e.g. the Handbook of Pharmaceutical Excipients (2$^{nd}$ Edition, Editors A. Wade and P. J. Weller; American Pharmaceutical Association; Washington; The Pharmaceutical Press; London, 1994). The mixture of the compounds according to the invention and the pharmaceutically acceptable auxiliary may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. nasal spray. For making dosage units, e.g. tablets, the use of conventional additives such as fillers, colorants, polymeric binders and the like is contemplated. In general any pharmaceutically acceptable additive which does not interfere with the function of the active compounds can be used. The compounds of the invention may also be included in an implant, a vaginal ring, a patch, a gel, and any other preparation for sustained release.

Suitable carriers with which the compositions can be administered include lactose, starch, cellulose derivatives and the like, or mixtures thereof used in suitable amounts.

Furthermore, the invention relates to the use of the non-steroidal compound according to the invention for the manufacture of a medicament for estrogen-receptor related treatments and treatment of estrogen-receptor related disorders such as peri- and/or post-menopausal complaints. Thus the invention also pertains to the medical indications of peri- and/or post-menopausal (climacteric) complaints and osteoporosis, i.e. a method of treatment in the field of hormone replacement therapy (HRT), comprising the administration to a patient, being a woman, of a compound as described hereinbefore (in a suitable pharmaceutical dosage form).

Further, the invention relates to the use of the non-steroidal compound according to the invention in the manufacture of a medicament having contraceptive activity. Thus the invention also pertains to the medical indication of contraception, i.e. a method of contraception comprising the administration to a subject, being a woman or a female animal, of a progestogen and an estrogen as is customary in the field, wherein the estrogen is a compound as described hereinbefore (in a suitable pharmaceutical dosage form).

Finally the invention relates to the use of the non-steroidal compound for the manufacture of a medicament having selective estrogenic and/or anti-estrogenic activity, such a medicament being generally suitable in the area of HRT (hormone replacement therapy).

The dosage amounts of the present compounds will be of the normal order for estrogenic compounds, e.g. of the order of 0.01 to 100 mg per administration.

The invention is further illustrated hereinafter with reference to some unlimitative examples and the corresponding formula schemes referred to. Compounds are identified by numbers (in bold letter type) with reference to the corresponding numbers in the schemes. Abbreviations used in the schemes: Me is methyl, Bn is benzyl, ph is phenyl, aryl represents the substituted phenyl as in formula 1.

EXAMPLES

Example 1

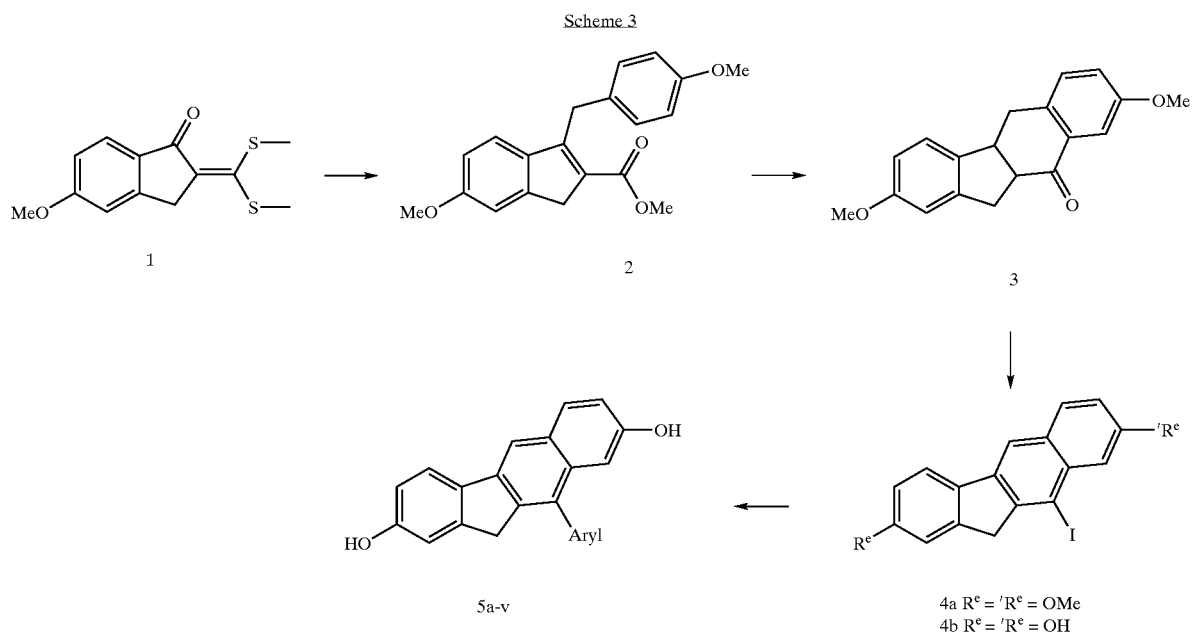

Preparation of precursor 10-iodo-2,8-dihydrox-11H-benzo[b]fluorene (4b). 59 ml 4-methoxybenzyl-magnesium chloride (0.2 M in diethyl ether) was added to 1 [J. V. Ram and M. Nath, *Indian J. Chem. Sect.B*; 34, 416–422 (1995)] (11.6 mmol) in 70 ml THF at 0° C. and the reaction mixture was stirred for 0.5 hour at 20° C. The mixture was poured into saturated aq. NH$_4$Cl, extracted with diethyl ether and dried over MgSO$_4$. After evaporation of the solvent the crude product was purified by chromatography on silica gel (heptane/ethyl acetate). The pure fractions were concentrated and the material obtained was taken up in 95 ml methanol and treated with BF$_3$.Et$_2$O (28 mmol). After 0.5 hour the temperature was raised to 65° C. and after 0.5 hour the reaction mixture was poured into water, extracted with CH$_2$Cl$_2$ and the organic layer washed with NaHCO$_3$ (aq). The extract was dried over MgSO$_4$, concentrated and the residue was recrystallised from methanol to afford pure 2 in 45% yield (Rf=0.48 heptane/ethyl acetate (3:2)).

A mixture of 2 (5 mmol) and palladium on carbon (10% Pd (w/w), 300 mg) in 120 ml ethanol/acetic acid (5:1) was stirred under an atmosphere of hydrogen for 1 hour. The catalyst was removed by filtration and the filtrate was concentrated.

The residue was dissolved in methanesulfonic acid and stirred at 90° C. for 15 minutes after which the mixture was poured into ice water and extracted with ethyl acetate. The organic layer was washed with NaHCO$_3$(aq) and dried over MgSO$_4$. Chromatography on silica gel (heptane/ethyl acetate) gave pure 3 in 85% yield. (Rf=0.49 heptane/ethyl acetate (2:1)); MP 96–98° C.

The compound 3 (0.34 mmol) was dissolved in ethanol and 1 ml hydrazine monohydrate was added. After 4 hours refluxing, water was added and the hydrazone was extracted with CH$_2$Cl$_2$. The organic layer was washed with water, dried and concentrated. The residue was taken up in 1.5 ml triethylamine and 0.2 g iodine in 0.7 ml THF was added at 0° C. After 1 hour the reaction mixture was diluted with toluene, poured into ice water and extracted with toluene. The organic layer was washed with 1N HCl and saturated NaHCO$_3$(aq), dried over MgSO$_4$ and concentrated. The residue was dissolved in 8 ml m-xylene/toluene (2:1) palladium on carbon (10% w/w, 100 mg) was added and the mixture was heated at 125° C. for 2 hours. After cooling the catalyst was filtered off, the filtrate was concentrated and the residue was purified on silica gel (heptane/ethyl acetate). The appropriate fractions were collected and concentrated to give pure 4a. Compound 4a was dissolved in 30 mL CH$_2$Cl$_2$ and treated with BBr$_3$ (3.5 mmol). After 1 hour another 2.1 mmol of BBr$_3$ was added. After 1.5 hours the mixture was carefully poured into sat. NaHCO$_3$ (aq) and extracted with ethyl acetate. The organic layer was dried over MgSO$_4$ and concentrated. Chromatography on silica gel (toluene/ethyl acetate) afforded pure 4b in 62% yield. (Rf=0.50 toluene/ethyl acetate (4:1)); ESI-MS: M+H=375.2, M−H=373.0.

General Procedure to Prepare Compounds 5a–v (10-aryl-2,8-dihydroxy-11H-benzo[b]fluorenes)

(reference to scheme 3)

A mixture of 10-iodo-benzofluorene derivative 4 (27 μmol), 3 mg Pd$_2$(dba)$_3$, 0.2 M Na$_2$CO$_3$(aq), 30 μmol arylboronic acid and 1 ml 2-methoxy-ethanol was heated for 5 hours at 55° C. Ethyl acetate and water were added to the reaction mixture and the organic layer was separated, dried over MgSO$_4$ and concentrated. The residue was purified on silica gel (toluene/ethylacetate) to give pure 5a–v (yields 14–52%).

| Compound | ARYL | Yield (%) | [M − H] |
|---|---|---|---|
| 5a | 4-chlorophenyl | 37 | [M − H] = 357.2 |
| 5b | 2-naphthyl | 44 | [M − H] = 373.2 |

-continued

| Compound | ARYL | Yield (%) | [M – H] |
|---|---|---|---|
| 5c | 3-methoxyphenyl | 32 | [M – H] = 353.4 |
| 5d | 3-trifluoromethylphenyl | 54 | [M – H] = 391.3 |
| 5e | 4-methylphenyl | 42 | [M – H] = 337.4 |
| 5f | 3-chloro-4-fluorophenyl | 40 | [M – H] = 375.2 |
| 5g | 3,4-methylenedioxophenyl | 49 | [M – H] = 367.4 |
| 5h | 4-phenylphenyl | 55 | [M – H] = 399.4 |
| 5i | 2-benzothiazole | 30 | [M – H] = 379.4 |
| 5j | 3-fluorophenyl | 27 | [M – H] = 341.4 |
| 5k | 4-methoxyphenyl | 27 | [M – H] = 353.4 |
| 5l | 4-fluorophenyl | 52 | [M – H] = 341.4 |
| 5m | 3,4-dichlorophenyl | 14 | [M – H] = 390.8 |
| 5n | 3-chlorophenyl | 37 | [M – H] = 357.0 |
| 5 | 4-trifluoromethylphenyl | 22 | [M – H] = 391.4 |
| 5p | 3-methylphenyl | 21 | [M – H] = 337.2 |
| 5q | 3-isopropylphenyl | 40 | [M – H] = 365.0 |
| 5r | 4-trifluoromethyloxyphenyl | 41 | [M – H] = 407.2 |
| 5s | 3-fluoro-4-phenylphenyl | 22 | [M – H] = 417.0 |
| 5t | 4-methylthiophenyl | 32 | [M – H] = 371.2 |
| 5u | 2-trifluoromethylphenyl | 20 | [M – H] = 391.0 |
| 5v | Phenyl | 25 | [M – H] = 323.2 |

Exampl 2 was dried over MgSO$_4$, concentrated and purified by chromatography on silica gel (heptane/ethyl acetate).

The purified product (0.43 mmol) was taken up in 2-methoxyethanol (16 ml) and Pd$_2$(dba)$_3$ (36 μmol), 3-hydroxyphenylboronic acid pinacolester (0.45 mmol) and Na$_2$CO$_3$ (2M in water, 2 ml) were added. The mixture was stirred for 30 minutes at 60° C., poured into water and extracted with ethyl acetate. The organic layer was dried over MgSO$_4$, concentrated and purified by chromatography on silica gel (CH$_2$Cl$_2$/methanol) to give pure 6 in 56% yield. (Rf=0.34 (heptane/ethyl acetate (7:3)).

A mixture of 6 (48 μmol), 1-(2-chloroethyl)pyrrolidine hydrochloride (76 μmol) and cesium carbonate (0.15 mmol) in acetonitrile (2 ml) was stirred for 3 hours at 50° C. The mixture was poured into water and extracted with ethyl acetate, the organic extract was dried over MgSO$_4$, the solvent evaporated and the residue was purified by chromatography on silica gel (CH$_2$Cl$_2$/methanol). The pure fractions were concentrated and the material obtained was dissolved in ethyl acetate (3 ml). Pd/C (10% w/w, 25 mg) and 3 drops of acetic acid were added and the mixture was stirred under an atmosphere of hydrogen for 5 hours. The catalyst was removed by filtration and the filtrate was concentrated. The residue was purified by chromatography

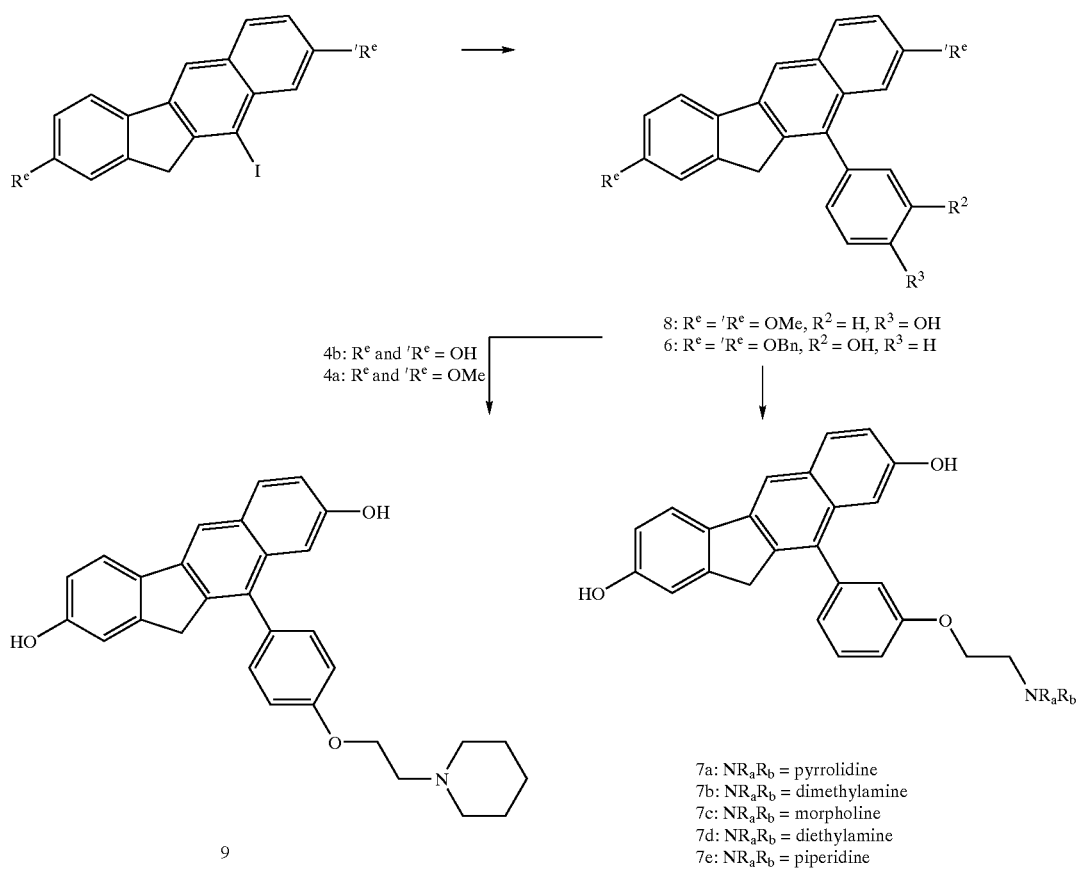

Scheme 4

8: R$^e$ = 'R$^e$ = OMe, R$^2$ = H, R$^3$ = OH
6: R$^e$ = 'R$^e$ = OBn, R$^2$ = OH, R$^3$ = H

4b: R$^e$ and 'R$^e$ = OH
4a: R$^e$ and 'R$^e$ = OMe

7a: NR$_a$R$_b$ = pyrrolidine
7b: NR$_a$R$_b$ = dimethylamine
7c: NR$_a$R$_b$ = morpholine
7d: NR$_a$R$_b$ = diethylamine
7e: NR$_a$R$_b$ = piperidine Compound 7a–d A mixture of 4b (0.94 mmol), potassium carbonate (3.0 mmol) and benzyl bromide (2.1 mmol) in acetone (10 ml) was refluxed overnight after which the mixture was poured into water and extracted with ethyl acetate. The organic layer on silica gel (CH$_2$Cl$_2$/methanol) to yield pure 7a in 22% yield. Rf=0.14 (CH$_2$Cl$_2$/methanol (9:1)), ESI-MS: M+H= 438.4, M–H=436.2.

Compound 7b

Compound 7b was prepared from 6 in 5% yield, in the same fashion as described for the preparation of 7a, using 2-dimethylaminoethyl chloride hydrochloride (Rf=0.18 CH$_2$Cl$_2$/methanol (9:1)); ESI-MS: M+H=412.4, M−H= 410.4.

Compound 7c

Compound 7c was prepared from 6 in 32% yield, in the same fashion as described for the preparation of 7a, using 1-(2-chloroethyl)morpholine hydrochloride instead of 1-(2-chloroethyl)pyrrolidine hydrochloride (Rf=0.21 CH$_2$Cl$_2$/methanol (9:1)); ESI-MS: M+H=454.4, M−H=452.2.

Compound 7d

Compound 7d was prepared from 6 in 65% yield, in the same fashion as described for the preparation of 7a, using 2-diethylaminoethyl chloride hydrochloride instead of 1-(2-chloroethyl)pyrrolidine hydrochloride (Rf=0.17 CH$_2$Cl$_2$/methanol (9:1)); ESI-MS: M+H=440.4, M−H=438.2.

Compound 7e

Compound 7e was prepared from 6 in 18% yield, as described for the preparation of 7a, using 1-(2-chloroethyl)piperidine hydrochloride instead of 1-(2-chloroethyl)pyrrolidine hydrochloride (Rf=0.15 CH$_2$Cl$_2$/methanol (9:1)); ESI-MS: M+H=452.4, M−H=450.2.

piperidine hydrochloride (0.2 mmol) were added and the mixture was refluxed for 3.5 hours. The reaction mixture was poured into water and extracted with ethyl acetate. The organic extract was dried over MgSO$_4$, concentrated and purified by chromatography on silica gel (toluene/methanol).

The pure fractions were collected and concentrated, the material obtained (46 μmol) was dissolved in CH$_2$Cl$_2$ and treated with ethanethiol (0.62 mmol) and aluminum chloride (95 μmol) at RT. After 16 hours the dark red mixture was poured into water and extracted with ethyl acetate. The organic extract was dried over MgSO$_4$, concentrated and purified by chromatography on silica gel (CH$_2$Cl$_2$/methanol) to give 9 in 22% yield. Rf=0.23 (toluene/methanol (85:15)), ESI-MS: M+H=452.4, M−H=450.2.

Example 3

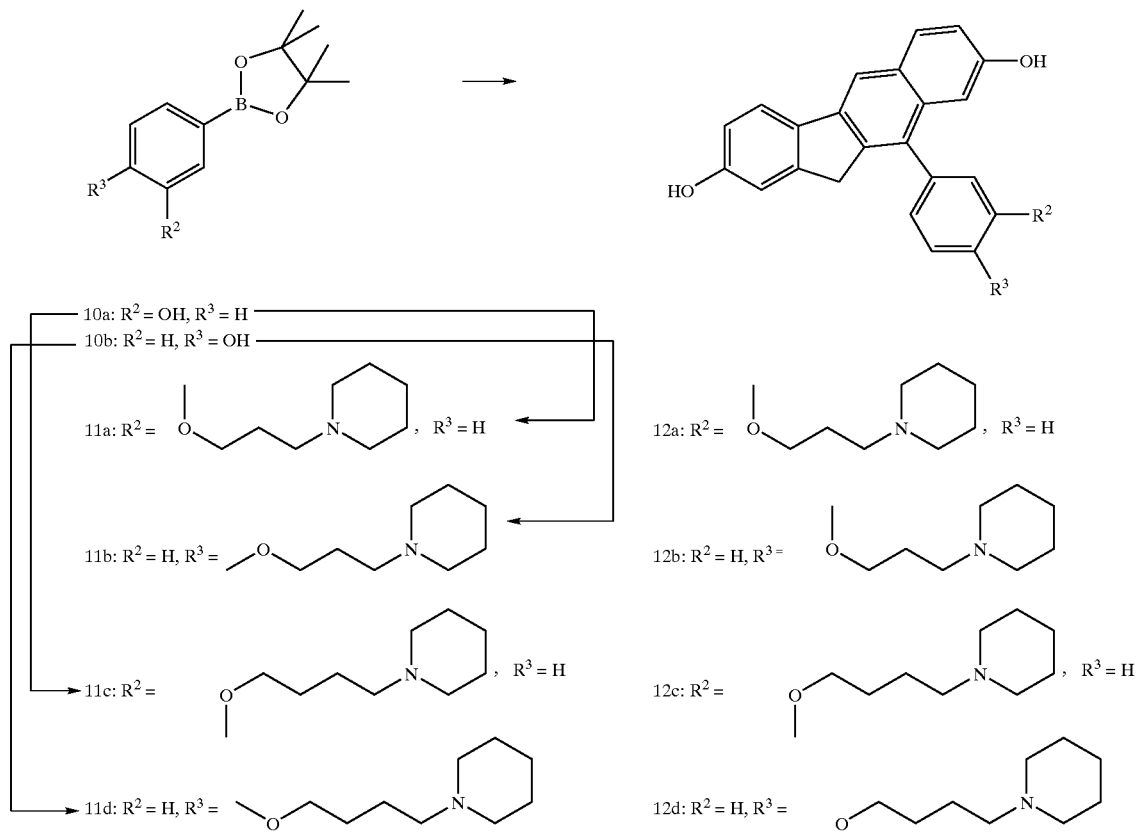

Scheme 5

Compound 9

A mixture of 4a (0.30 mmol), Pd$_2$(dba)$_3$ (0.40 μmol), 4-hydroxyphenylboronic acid (0.30 mmol) and sodium carbonate (2 M in water, 4 ml) in 12 ml 2-methoxyethanol was stirred at 60° C. After 30 minutes the mixture was poured into water and extracted with ethyl acetate. The organic extract was dried over MgSO$_4$, concentrated and purified by chromatography on silica gel (toluene/ethyl acetate) to give 8 in 65% yield. Rf=0.24 (toluene/ethyl acetate (8:2)).

Compound 8 (0.16 mmol) was dissolved in toluene (3 ml). Sodium hydride (0.4 mmol) and 1-(2-chloroethyl)

Compound 12a

A mixture of 3-hydroxyphenylboronic acid pinacolester 10a (0.68 mmol), cesium carbonate (0.68 mmol) and 1-bromo-3-chloropropane (0.80 mmol) in acetonitrile (3 ml) was stirred overnight at RT. Additional cesium carbonate (0.31 mmol) and 1-bromo-3-chloropropane (0.4 mmol) were added and the mixture was stirred overnight at 60° C. The mixture was poured into water and extracted with CH$_2$Cl$_2$. The CH$_2$Cl$_2$-layer was dried over MgSO$_4$, concentrated and purified by chromatography on silica gel (toluene/ethyl acetate). The purified product was dissolved in piperidine and stirred for 48 hours at 45° C. The solid material (piperidine.HCl) was filtered off and the filtrate was concentrated to give 11a in 88% yield. Rf=0.05 (toluene/ethyl acetate (4:1)).

A mixture of 4b (67 μmol), 11a (86 μmol), PdCl₂(dppf)₂ (5 μmol) and sodium carbonate (2 M in water, 0.25 ml) in 2.5 ml 2-methoxyethanol was stirred at 90° C. After 2 hours the mixture was poured into water and extracted with ethyl acetate. The organic extract was dried over MgSO₄, concentrated and purified by chromatography on silica gel (CH₂Cl₂/methanol). The appropriate fractions were collected and concentrated, the material obtained was recrystallised from CHCl₃ to give 12a in 38% yield. Rf=0.42 (CH₂Cl₂/methanol (85:15)).

Compound 12b

A mixture of 4-hydroxyphenylboronic acid pinacolester 10b (0.68 mmol), potassium hydroxide (2.1 mmol) and 1-bromo-3-chloropropane (2.8 mmol) in methanol (2 ml) was refluxed for 24 hours. The mixture was poured into water and extracted with ethyl acetate. The organic extract was dried over MgSO₄, concentrated and purified by chromatography on silica gel (toluene/ethyl acetate). The purified product was dissolved in piperidine and stirred overnight at 50° C. The solid material (piperidine.HCl) was filtered off and the filtrate was concentrated to give 11b in 80% yield. Rf=0.10 (toluene/methanol (9:1)).

Compound 12b was prepared from 4a and 11b in 20% yield, in a similar fashion as described for the preparation of 12a. Rf=0.42 (CH₂Cl₂/methanol (85:15)), ESI-MS: M+H= 466.4, M−H=464.6.

Compound 12c

Compound 12c was prepared from 10a in 25% yield, as described for the preparation of 12a, using 1-bromo-4-chloro-butane instead of 1-bromo-3-chloro-propane. Rf=0.21 (CH₂Cl₂/methanol (8:2)), ESI-MS: M+H=480.6, M−H=478.2.

Compound 12d

To mixture of 1,4-diiodobutane (5 mmol) and cesium carbonate (0.68 mmol) in acetonitrile (2 ml) was portionwise added 4-hydroxyphenylboronic acid pinacolester 11b (0.68 mmol) at 40° C. After 2.5 hours water was added and the mixture was extracted with ethyl acetate. The organic layer was dried over MgSO₄, concentrated and purified by chromatography on silica gel (heptane/toluene). The purified product was dissolved in piperidine and stirred at RT for 2 hours. The solid material (piperidine.HI) was filtered off and the filtrate was concentrated to give 11d in 32% yield. Rf=0.55 (toluene/methanol (8:2)).

Compound 12d was prepared from 4b and 11d in 13% yield, in a similar fashion as described for the preparation of 12a. Rf=0.22 (CH₂Cl₂/methanol (8:2)), ESI-MS: M+H= 480.4, M−H=478.2.

Example 4

Scheme 6

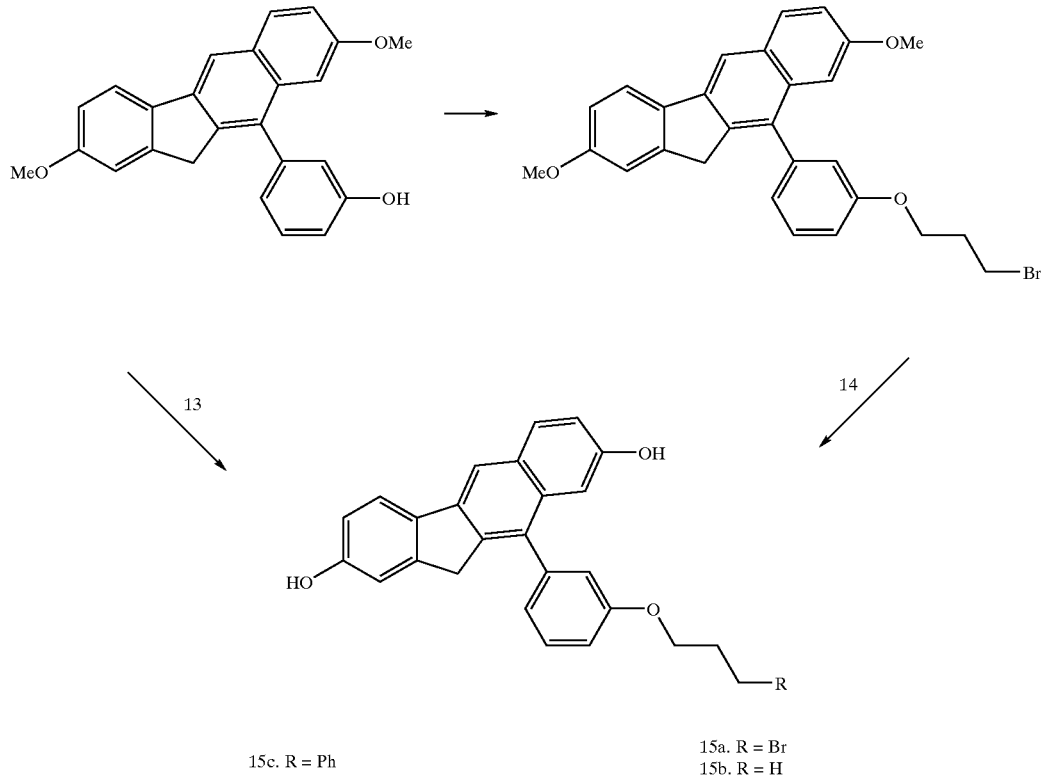

15a. R = Br
15b. R = H
15c. R = Ph

Compound 14

A mixture of 2.03 mmole of 1,3-dibromopropane and 1.02 mmole of potassium carbonate in 10 ml of acetone was warmed to 40° C. To this solution 0.51 mmole of 13 in 10 ml of acetone was added dropwise and the reaction mixture was stirred at 40° C. for 23 hours. An additional mixture of 2.03 mmole of 1,3-dibromopropane and 1.02 mmole of potassiumcarbonate in 5 ml of acetone was added and the reaction mixture stirred for 4 hours at reflux temperature. The reaction mixture was taken up in ethyl acetate and water, washed with water and saturated NaCl solution, dried over MgSO₄ and concentrated. The crude product was purified by chromatography on silica gel (heptane/ethyl acetate) to give pure 14 in 65% yield.

Rf=0.64 (heptane/diethylether (7:3)).

Compound 15a

82 μmole of 14 was dissolved in 6 ml of dry CH$_2$Cl$_2$. 327 μmole of BF$_3$.S(CH$_3$)$_2$ was added and the solution was stirred at room temperature for 16 hours. The reaction mixture was taken up in ethyl acetate, washed with water and saturated NaHCO$_3$ solution, dried over MgSO$_4$ and concentrated. The crude product was purified by chromatography on silica gel (CH$_2$Cl$_2$/methanol) to give pure 15a in 93% yield.

Rf=0.47 (CH$_2$Cl$_2$/methanol (9:1)).

Compound 15b

22 μM of bromide 14 was refluxed for 1.5 hours with 100 μm LiAlH$_4$ in THF. Water and ethyl acetate were added to the reaction mixture and the organic layer was separated, dried over MgSO$_4$ and concentrated. The residue was purified on silicagel (methylene/methanol) to give pure 3'-O-propyl compound 15b in yield 37%. Rf=0.40 (heptane-ethyl acetate 7:3).

Compound 15c

54 μm of compound 13 was reacted with 1.7 mM 1-bromo-3-phenylpropane in the presence of 1.7 mM K$_2$CO$_3$ in 3 ml acetone at room temperature. After 24 hours the salts were removed by filtration. The filtrate was concentrated and redissolved in methylene chloride. The mixture was extracted with water, dried over MgSO$_4$ and concentrated. The residue was purified by chromatography on silica gel (heptane/ethylacetate). (yield=88%).

47 μm of the resulting product was demethylated with 1.9 mM (CH$_3$)$_3$S.BF$_3$ in CH$_2$Cl$_2$ for one night. Ethyl acetate and water were added to the reaction mixture and the organic layer was separated, dried over MgSO$_4$ and concentrated. The residue was purified on silica gel (heptane/ethylacetate) to give pure compound 15c in yield=57%. Rf 0.7 (heptane ethyl acetate 8:2).

Example 5

Scheme 7

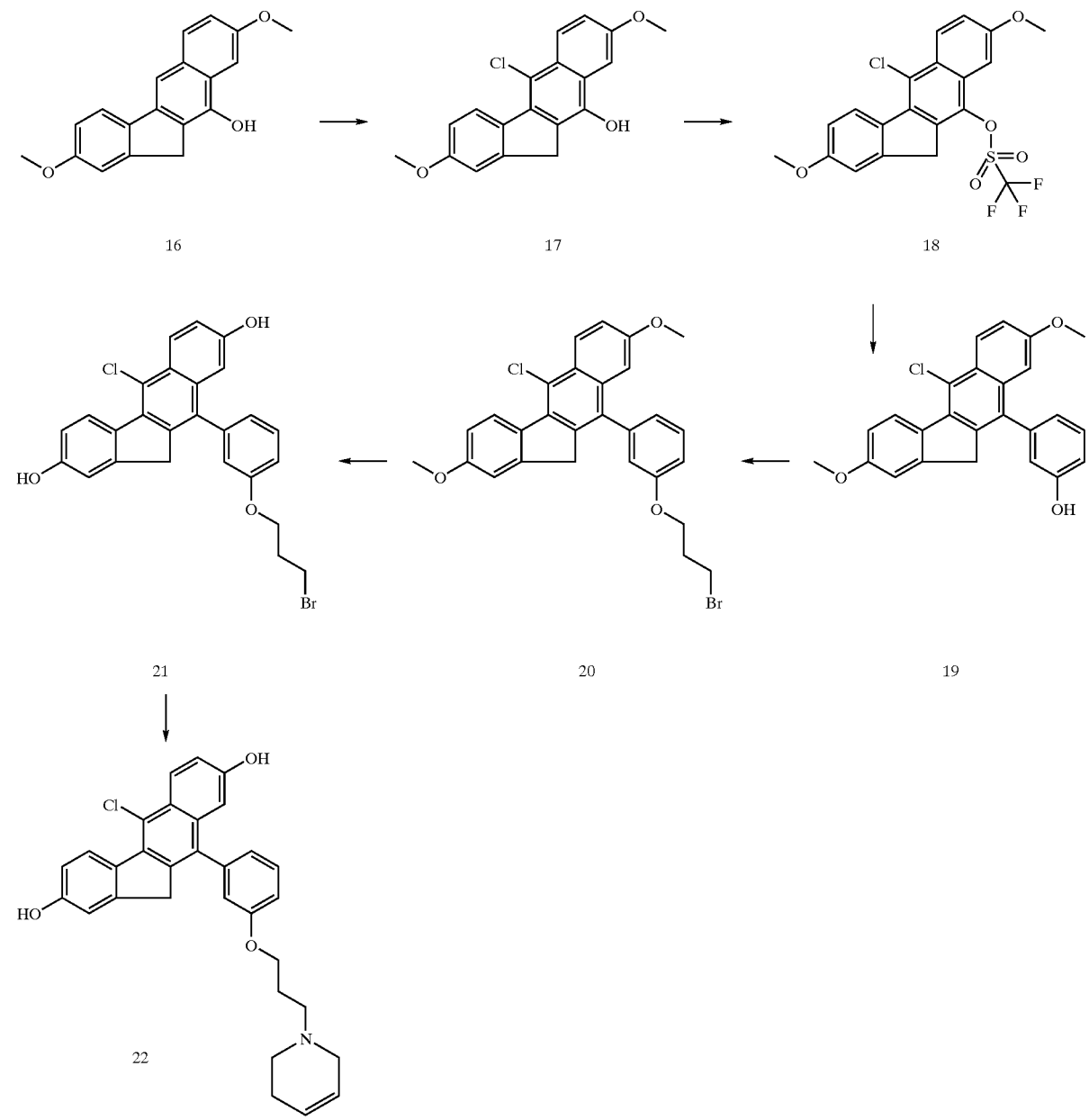

2,8-dimethoxy-10-hydroxy-11H-benzo[b]fluorene (Compound 16)

The compound 2,8-dimethoxy-10-hydroxy-11H-benzo[b] fluorene (Compound 16) 1 was prepared from its corresponding ester as explained above for step 4 in scheme 1. An amount of 3 g of the corresponding unsaturated ester was added in small portions over a few minutes to 30 ml of methanesulphonic acid at 60° C. After stirring for ½ hr the cyclization was complete. The mixture was then poured onto ice water and stirred for an additional ½ hr. The product was filtered, washed with water and thoroughly dried over $P_2O_5$, to give 2.2 gr of compound 16.

$R_f$ 0.38 (heptane/eth. ac. 7/3). NMR (DMSO) 3.82, 3.88 (2×3, s, $OCH_3$), 3.95 (s, 2, $CH_2$). 9.57 (s, 1, OH), 6.97, 7.11, 7.20, 7.55, 7.51, 7.75, 7.80 (7H's, aromatic protons).

5-chloro-2,8-dimethoxy-10-hydroxy-11H-benzo[b]fluorene (Compound 17)

To a solution of 800 mg of compound 16 in 10 ml of DMF was added 850 mg of 2,2,3,4,5,6-hexachlorocyclohexa-3,5-diene in small portions over 5 minutes. The mixture was stirred for 1 hr and then poured into 50 ml of water. The dark reaction product was extracted with ethyl acetate and purified by chromatography over silica gel (heptane/ethyl acetate as eluent), to provide 380 mg of 17 as a brown solid; $R_f$ 0.38 (hept./ethyl ac. 6/4), $R_f$ (starting material) 0.44. NMR (DMSO) 3.85, 3.92 (2×s, 6, $OCH_3$) 4.03 (s, 2, $CH_2$), 7.03, 7.30, 8.13, 8.38 (2×AB, 4, Ar—H), 7.25, 7.61 (2×br.s, 2, Ar—H).

Compound 18

To a solution of 900 mg of 17 in 8 ml of pyridine was added at 0° C. 700 μl of trifluoromethanesulphonic anhydride. Stirring was performed for 1 hr at RT followed by pouring into water and additional stirring for 15 min. followed by filtration of the crude product. Purification was achieved by chromatography over silicagel, to provide 800 mg of triflate 18; Mp 165–168° C. NMR ($CDCl_3$) 3.90, 3.96 (2×s, 6, $OCH_3$), 4.18 (s, 2, $CH_2$), 7.0, 7.09, 7.29, 7.35, 8.11, 8.47 (6H, Ar—H).

Compound 19

A mixture of 210 mg of triflate 18, 220 mg of 3-hydroxyphenyl-pinacolborane, 200 mg of $K_3PO_4$, 15 mg of $As(PPh)_3$, 15 mg of $PdCl_2.PPh_3$, 0.5 ml of water and 5 ml of dioxane was heated at 100° C. for 1,5 hr under a nitrogen atmosphere. The reaction was poured into water and extracted with ethyl acetate. Chromatography of the resulting material provided 215 mg of 19 as an amorphous product; $R_f$ 0.35 (hept./ethyl ac. 7/3), Mp 184–185° C. NMR ($CDCl_3$) 3.74, 3.87 (s, 6, $OCH_3$), 3.80 (s, 2, $CH_2$), 6.82–7.0 (m, 6, Ar—H), 7.25, 7.40, 8.38, 8.53 (4H, Ar—H).

Compound 20

A mixture of 200 mg of 19, 500 mg of powdered $K_2CO_3$, 1.25 ml of 1,3-dibromopropane and 10 ml of acetonitrile was heated at 55° C. for 3 hr.

The reaction was diluted with water and extracted with ethyl acetate. The crude product was purified by chromatography on silica gel (hept./ethyl acetate), to provide 220 mg of 20; $R_f$ 0.63 (hept./eth.ac. 7/3); NMR ($CDCl_3$) 3.65 (t, 3, $CH_2Br$), 2.33 (m, 2, $CH_2$), 4.13 (t, 2, $CH_2O$), 3.78 (s, 2, $CH_2$).

Compound 21

To a solution of 220 mg of 20 in 7 ml of methylenechloride was added 1.5 ml of $BF_3$.dimethylsulfide complex. The mixture was stirred until completion of the reaction (5 hr). The reaction was poured into water and the product extracted with ethyl acetate. Chromatography provided 210 mg of 21 as a colorles amorphous material; $R_f$ 0.25 (hept./eth.ac. 7/3). NMR ($CDCl_3$) 3.67 (t, 3, $CH_2Br$), 2.33 (m, 2, $CH_2$), 4.15 (t, 2, $CH_2O$), 3.77 (s, 2, $CH_2$).

Compound 22

A mixture of 70 mg of 21, 0.3 ml of 1,2,5,6-tetrahydropyridine and 3 ml of acetonitrile was heated at 55° C. for ½ hr. The mixture was then poured onto 5% $NaHCO_3$ and extracted with ethyl acetate. The product was purified by passing through a short silica column ($CH_2Cl_2/CH_3OH$). The product thus obtained was converted into a HCl salt by treatment of a solution the free base in methanol/ether with 1M HCl/ether. The hydrochloride salt thus obtained was freeze-dried from water to obtain 45 mg of amorphous 22. NMR (DMSO) 9.77, 9.82 (2×s, 2, OH's), 5.70 and 5.88 (2×m, 2, tetrahydropyridine), 8.32, 8.20, 7.52, 7.21, 7.08, 6.98, 6.87 (10, aromatic H's).

Example 6

Scheme 8

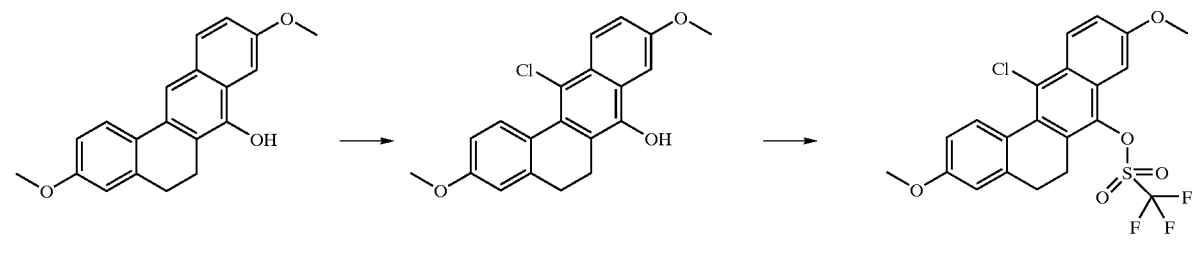

23      24      25

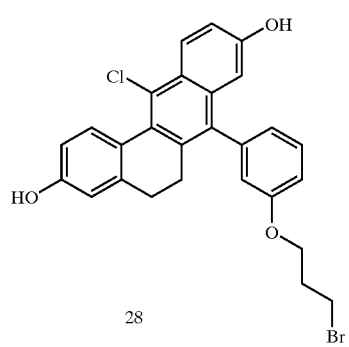

28

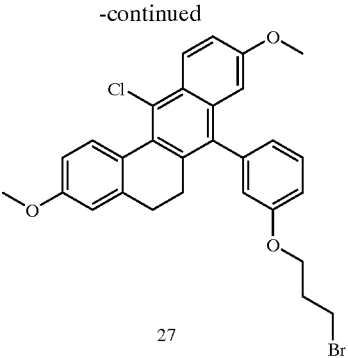

27

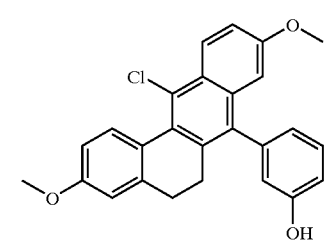

26

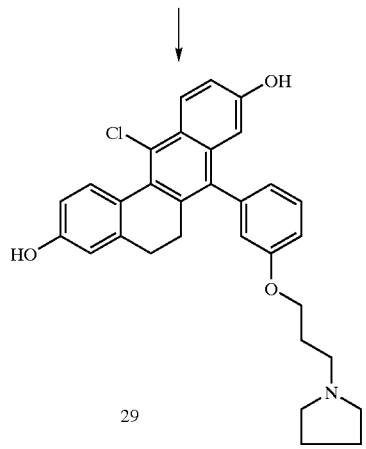

29

3,9-dimethox-7-hydroxy-5,6-dihydro-benz[a]anthracene (Compounds 23) and 12-chloro-3,9-dimethoxy-7-hydroxy-5,6-dihydro-benz[a]anthracene (Compound 24).

The compound 3,9-dimethoxy-7-hydroxy-5,6-dihydro-benz[a]anthracene (compounds 23) was prepared analogously to compound 16 in example 5. To a solution of 600 mg of 23 in 10 ml of DMF was added in portions 600 mg of 2,3,4,4,5,6-hexachlorocyclohexa-2,5-dien-1-one. The mixture was then stirred at 40° C. for 4 hr. Then the reaction was poured into water and the product extracted with ethyl acetate. The crude material was passed through a silicagel column (hept./eth.ac.) and finally triturated with heptane-diisopropyl ether to provide 280 mg of 24 as orange crystals; Mp 140–141° C., $R_f$ 0.28 (hept./eth.ac. 7/3) starting material $R_f$ 0.30.

Compound 25

To a solution of 300 mg of 24 in 3 ml of pyridine was added 200 gl of triflic anhydride. The mixture was stirred for 1 hr at rt, and then poured into water and extracted with ethyl acetate. The product was purified over silica gel and afforded 220 mg of 25 as a white solid; Mp 122–124; $R_f$ 0.70 (hept./ethyl ac. 7/3).

Compound 26

A mixture of 210 mg of 25, 220 mg of 3-hydroxyphenylpinacolborane, 200 mg of $K_3PO_4$ 15 mg of (PPh$_3$)As, 15 mg of PdCl$_2$(PPh$_3$)$_2$, 0.5 ml of water and 5 ml of dioxane was heated at 100° C. for 1.5 hr. The mixture was then poured into water and extracted with ethyl acetate. Chromatography over silica gel provided 215 mg of 26 as an oil; $R_f$ 0.28 (hept./ethyl acetate 7/3). NMR (DMSO) 2.56 (4, CH$_2$CH$_2$), 3.67, 3.80 (2×s, 6, OCH$_3$), 8.32, 8.18, 7.33, 6.93, 6.70 (10, Ar—H's), 9.64 (s, 1, OH).

Compound 27

A mixture of 215 mg of 26, 500 mg of K$_2$CO$_3$, 1.2 ml of 1,3-dibromopropane and 10 ml of acetonitrile was heated at 55° C. for 2.5 hr. The reaction was then poured in water and extracted with ethyl acetate. Chromatography provided 220 mg of 27 as a colorles oil ; $R_f$ 0.60 (hept./ethyl acetate 7/3). NMR (CDCl$_3$) 2.60 (m, 4, CH$_2$CH$_2$), 2.30 (m, 2, CH$_2$), 3.60 (t, 2, CH$_2$Br), 4.13 (t, 2, CH$_2$O), 3.72, 3.87 (2×s, 6, OCH3).

Compound 28

To a solution of 190 mg of 27 in 7 ml of methylenechloride was added 1.5 ml of BF$_3$.dimethylsulfide complex. After stirring at rt for 4 hr the mixture was poured onto water and extracted with ethyl acetate. Chromatography of the crude product gave 150 mg of essentially pure 28; $R_f$ 0.20 (hept./ethyl ac. 7/3); NMR (DMSO) 2.27 (m, 2, CH$_2$), 2.50 (m, 4, CH$_2$CH$_2$), 3.68 (t, 2, CH$_2$Br), 4.12 (t, 2, CH$_2$O), 9.68, 9.82 (2×s, 2, OH).

Compound 29

A mixture of 60 mg of 28, 0.4 ml of pyrrolidine and 3 ml of acetonitrile was stirred at 50° C. for ½ hr. The mixture was then poured into 5% NaHCO$_3$ and extracted with ethyl acetate. The product was purified by passing through a short silica column (CH$_2$Cl$_2$/CH$_3$OH as eluent) and then converted into a HCl salt by treatment with 1M HCl/ether. The resulting hydrochloride was freeze dried from water to give 35 mg of 29; $R_f$ 0.20 (CH$_2$Cl$_2$/CH$_3$OH/HOAc 90/10/1); NMR (DMSO) 9.70 and 9.82 (2×s, 2H, OH's), 8.22, 8.05, 7.48, 7.17, 7.06, 6.88, 6.84, 6.76, 6.70, 6.62 (m, 1OH, Ar—H's), 4.10 (t, 2, CH$_2$O).

Example 7

Scheme 9

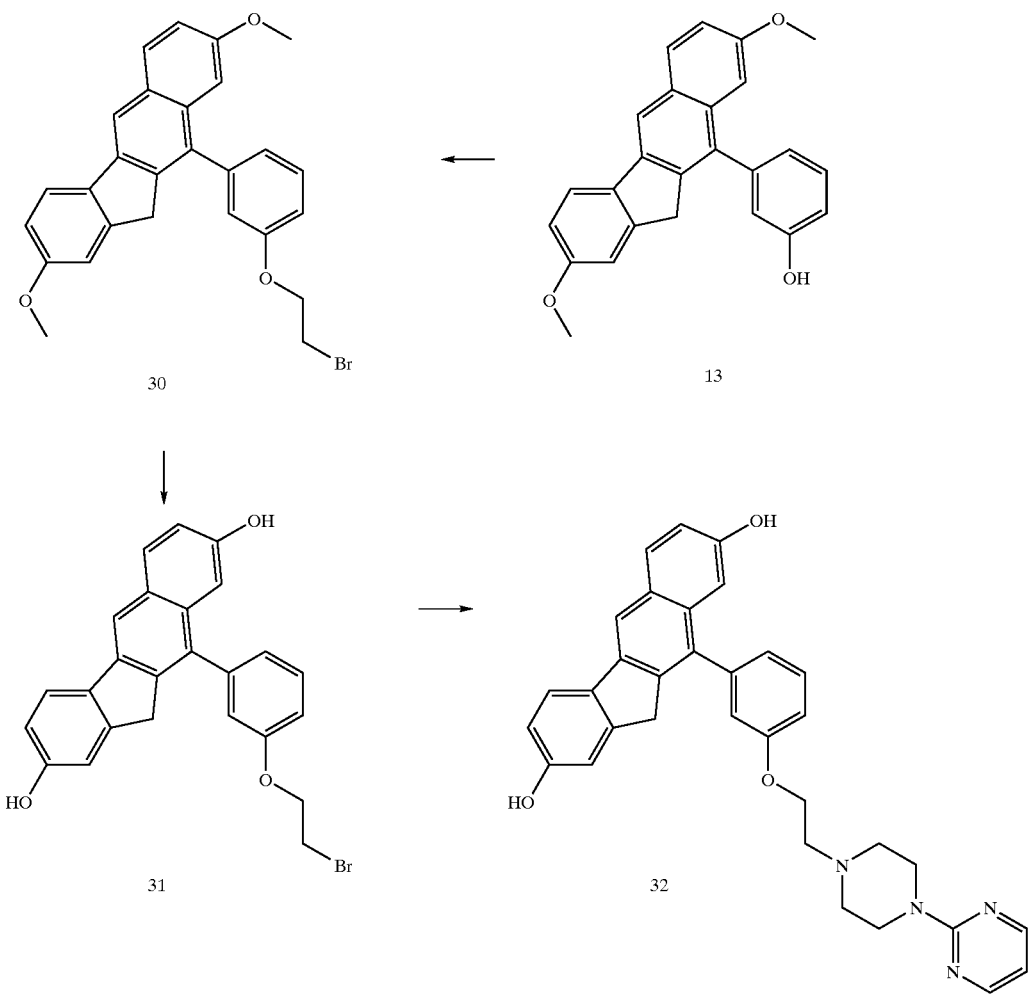

Compound 30

A mixture of 300 mg of compound 13, 900 mg of powdered $K_2CO_3$, 2 ml of 1,2-dibromopropane and 8 ml of acetonitrile was heated at 55° C. for 16 hr. The reaction was diluted with water and extracted with ethyl acetate. The crude product was purified by chromatography on silica gel (hept./ethyl acetate), to provide 310 mg of 30; $R_f$ 0.50 (hept./eth.ac. 7/3); NMR ($CDCl_3$) 3.67 (t, 3, $CH_2Br$), 4.35 (t, 2, $CH_2O$), 3.79 (s, 2, $CH_2$), 3.75, 3.87 (2×s, 6, $OCH_3$).

Compound 31

To a solution of 310 mg of 30 in 6 ml of methylenechloride was added 2 ml of $BF_3$.dimethylsulfide complex. The mixture was stirred until completion of the reaction (5 hr). The reaction was poured into water and the product extracted with ethyl acetate. Chromatography provided 290 mg of 31 as a colorles amorphous material; $R_f$ 0.19 (hept./eth.ac. 7/3). NMR ($CDCl_3$) 3.67 (t, 3, $CH_2Br$),), 4.35 (t, 2, $CH_2O$), 3.76 (s, 2, $CH_2$).

Compound 32

A mixture of 60 mg of 31 0.3 g of 2-pyrimidinylpiperazine and 2 ml of acetontrile was heated at 50° C. for 16 hr. The mixture was then diluted with water and the product extracted with ethyl acetate. The organic material was passed through a short silica column (a gradient of $CH_2Cl_2$/ $CH_3OH$ as eluent), to provide essentially pure 32 as the free base. This was dissolved in a small amount of ethyl acetate and treated with 1M HCl in ether to give the HCl salt. This was freeze dried from water to provide 48 mg of amorphous HCl salt of 32. $R_f$ 0.82 ($CH_2Cl_2$—$CH_3OH$— acetic acid 9/1/0,1); NMR (DMSO) 4.50 (m, 2, $CH_2O$), 6.76, 6.84, 6.88, 6.96, 7.05, 7.09, 7.16, 7.21, 7.55, 8.21, 8.32, 8.44 (resp. 1H, 1H, 1H, 1H, 1H, 1H, 1H, 1H, 1H, 1H, 1H, 2H's; Ar—H's).

Example 8

Biological Activity

Determination of competitive binding to cytoplasmic human estrogen receptor α or β from recombinant CHO cells is used to estimate the relative affinity (potency ratio) of a test compound for estrogen receptors present in the cytosol of recombinant Chinese hamster ovary (CHO) cells, stably transfected with the human estrogen receptor α (hERα) or β receptor (hERβ), as compared with 17β-estradiol ($E_2$).

The estrogenic and antiestrogenic activity of compounds is determined in an in vitro bioassay with recombinant Chinese hamster ovary (CHO) cells stably co-transfected with the human estrogen receptor α (hERα) or β receptor (hERβ), the rat oxytocin promoter (RO) and the luciferase reporter gene (LUC). The estrogenic activity (potency ratio) of a test compound to stimulate the transactivation of the enzyme luciferase mediated via the estrogen receptors hERα or hERβ is compared with the standard estrogen estradiol. The antiestrogenic activity (potency ratio) of a test compound to inhibit the transactivation of the enzyme luciferase mediated via the estrogen receptors hERα or hERβ by the estrogen estradiol is compared with the standard ICI 164.384 (=(7α,17β)-N-butyl-3,17-dihydroxy-N-methylestra-1,3,5(10)-triene-7-undecanamide).

Results

| Compound | ERβ antagonism | Compound | ERβ antagonism |
|---|---|---|---|
| 5a | + | 5s | + |
| 5b | + | 5t | + |
| 5c | + | 5u | ++ |
| 5d | + | 5v | + |
| 5e | ++ | 7a | +++ |
| 5f | + | 7b | +++ |
| 5g | + | 7c | +++ |
| 5h | + | 7d | +++ |
| 5I | + | 7e | +++ |
| 5j | + | 9 | ++ |
| 5k | + | 12a | +++ |
| 5l | ++ | 12b | ++ |
| 5m | ++ | 12c | +++ |
| 5n | + | 12d | + |
| 5o | + | 14 | ++ |
| 5p | + | 17a | +++ |
| 5q | + | 17b | ++ |
| 5r | ++ | 17c | ++ |

5 > 5% (relative to ICI): +
> 40%: ++
>100%: +++

What is claimed is:

1. A compound having the formula 1:

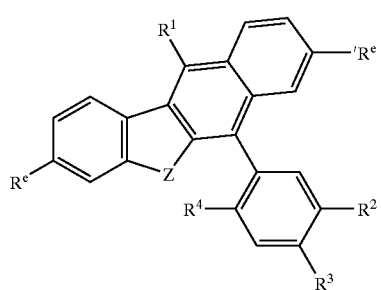

Formula 1 wherein, $R^e$ and $'R^e$ are OH, optionally independently etherified or esterified;

Z is —CH$_2$— or —CH$_2$CH$_2$—;

$R^1$ is H, halogen, CF$_3$, or (1C–4C)alkyl;

$R^2$, $R^3$ and $R^4$ are independently H, halogen, —CF$_3$, —OCF$_3$, (1C–8C)Alkyl, hydroxy, (1C–8C)alkyloxy, aryloxy, aryl(1C–8C)alkyl, halo(1C–8C)alkyl, —O(CH$_2$)$_m$X, wherein X is halogen or phenyl and m=2–4; —O(CH$_2$)$_m$NR$_a$R$_b$, —S(CH$_2$)$_m$NR$_a$R$_b$ or —(CH$_2$)$_m$NR$_a$R$_b$, wherein m=2–4 and R$_a$, R$_b$ are independently (1C–8C)alkyl, (2C–8C)alkenyl, (2C–8C) alkynyl, or aryl, optionally substituted with halogen, —CF$_1$, —OCF$_3$, —CN, —NO$_2$, —OH, (1C–8C) alkoxy, aryloxy, carboxyl, (1C–8C)alkylthio, carboxylate, (1C–8C)alkyl, aryl, aryl(1C–8C)alkyl, halo(1C–8C)alkyl or R$_a$ and R$_b$ form a 3–8 membered ring structure, optionally substituted with halogen, —CF$_3$, —OCF$_3$, —CN, —NO$_2$, hydroxy, hydroxy (1C–4C)alkyl, (1C–8C)alkoxy, aryloxy, (1C–8C) alkylthio, carboxyl, carboxylate, (1C–8C)alkyl, aryl, aryl(1C–8C)alkyl, halo(1C–8C)alkyl.

2. The compound according to claim 1, wherein Z is —CH$_2$— and $R^4$ is H.

3. The compound according to claim 1, wherein $R^2$ is H, halogen or CF$_3$.

4. The compound according to claim 1, wherein $R^1$ is halogen.

5. The compound according to claim 2, wherein, $R^1$ is H;

$R^3$ is H;

$R^2$ is (3C–6C)alkyloxy, —O(CH$_2$)$_m$X, wherein X is halogen or phenyl and m=2–3, or —O(CH$_2$)$_m$NR$_a$R$_b$, wherein m=2–3 and R$_a$, R$_b$ are independently (1C–5C) alkyl or (3C–5C)alkenyl, optionally substituted with OH or methoxy, or R$_a$ and R$_b$ form a 4–7 membered ring structure selected from the list: azetidine, pyrrolidine, 3-pyrroline, piperidine, piperazine, tetrahydropyridine, morpholine, thiomorpholine, thiazolidine, homopiperidine, tetrahydroquinoline and 6-azabicyclo[3.2.1]octane, which 4–7 membered ring structure can optionally be substituted with OH, hydroxy(1C–2C)alkyl, methoxy, acetyl, carboxylate, (1C–3C)alkyl, phenyl, benzyl, and phenylethyl.

6. A pharmaceutical composition, comprising:
the compound according to claim 1, and
a pharmaceutically acceptable carrier.

7. A method of treating a patient in need of an estrogen-receptor related therapy, comprising:
administering a effective amount of the compound according to claim 1, wherein the estrogen-receptor related therapy is selected from the group consisting of contraception, treatment of benign prostate hypertrophy, cardiovascular disorders, peri and/or post-menopausal complaints, osteoporosis, estrogen dependent tumor control and central nervous system disorders.

8. The method according to claim 7, wherein the estrogen-receptor related therapy is hormone replacement therapy.

9. A method of antagonizing an ERβ-receptor, comprising:
administering a effective amount of the compound according to claim 1 to sufficiently antagonize the ERβ-receptor.

10. A method of inducing an ERβ receptor antagonist affect in a patient in need thereof, comprising:
administering a effective amount of the compound according to claim 1 to sufficiently antagonize the ERβ-receptor.

* * * * *